(12) United States Patent
Beselt

(10) Patent No.: US 7,899,281 B2
(45) Date of Patent: Mar. 1, 2011

(54) LARGE AMPLITUDE HIGH FREQUENCY OPTICAL DELAY

(75) Inventor: Ronald E. Beselt, Burnaby (CA)

(73) Assignee: Honeywell ASCa Inc., Mississauga (CA)

(*) Notice: Subject to any disclaimer, the term of this patent is extended or adjusted under 35 U.S.C. 154(b) by 393 days.

(21) Appl. No.: 12/168,906

(22) Filed: Jul. 8, 2008

(65) Prior Publication Data
US 2010/0007955 A1    Jan. 14, 2010

(51) Int. Cl.
*G02B 5/12* (2006.01)
*G02B 6/24* (2006.01)

(52) U.S. Cl. ........ 385/24; 385/48; 359/212.1; 359/213.1; 359/873

(58) Field of Classification Search ............ 385/24, 385/25, 27, 31, 48; 359/197.1, 198.1, 212.1, 359/213.1, 214.1, 220.1, 221.1, 221.2, 223.1, 359/225.1, 520, 522, 529, 873, 877; 398/53, 398/102, 161
See application file for complete search history.

(56) References Cited

U.S. PATENT DOCUMENTS

| | | | |
|---|---|---|---|
| 3,776,637 A | 12/1973 | Hecht | |
| 5,220,463 A | 6/1993 | Edelstein et al. | |
| 6,147,799 A * | 11/2000 | MacDonald | 359/380 |
| 6,747,736 B2 | 6/2004 | Takahashi | |
| 6,979,088 B2 | 12/2005 | Currie | |
| 7,046,412 B2 * | 5/2006 | Dorney | 359/226.1 |
| 7,239,775 B2 * | 7/2007 | Xu et al. | 385/25 |
| 7,239,809 B2 | 7/2007 | Pescod | |
| 7,453,619 B2 * | 11/2008 | Kim et al. | 359/226.1 |
| 2006/0109519 A1 | 5/2006 | Beselt et al. | |
| 2007/0091400 A1 * | 4/2007 | Dufour et al. | 359/196 |
| 2008/0259428 A1 * | 10/2008 | Zimdars et al. | 359/211 |
| 2010/0157403 A1 * | 6/2010 | Lai | 359/198.1 |

OTHER PUBLICATIONS

Product Brochure, Model ODL-150 Scaning Optical Delay Line, May 8, 2000, Clark-MXR, Inc., US.

* cited by examiner

*Primary Examiner* — Frank G Font
(74) *Attorney, Agent, or Firm* — Cascio Schmoyer & Zervas

(57) ABSTRACT

Optical delay line system that includes a retro-reflection mirror which is displaced along a circular path while being maintained in angular alignment with launch and return sources of light subject the components of the system to minimum levels of unbalanced linear acceleration. A retroreflector is pivotally mounted on a rotating element such that the optical axis of the retroreflector's motion is mobile such that its angle or position changes relative to a fixed observer. There is no linear stopping and starting of the retroreflector and all acceleration of the retroreflector is rotational acceleration with small angles so the required forces in the optical delay line are greatly reduced. Both large displacement and high repetition rates are achieved. The system can be configured so that optical fibers serve as launch and return optics. Alternatively, free space beam paths deliver light to the optical delay and return the reflected light from the retroreflector.

20 Claims, 4 Drawing Sheets

LARGE AMPLITUDE HIGH FREQUENCY OPTICAL DELAY

FIELD OF THE INVENTION

The present invention relates generally to optical delay line apparatuses that include a retro-reflection mirror, which is displaced along a circular path while being maintained in angular alignment with the launch and return sources of light such as optical fibers. With this arrangement, the component parts of the apparatus are subject to minimum levels of unbalanced linear acceleration. The apparatus achieves both large displacement and high repetition rates.

BACKGROUND OF THE INVENTION

Optical delay lines are an essential part of most time-resolved optical experiments, including time-domain terahertz technology, ultrafast optics research, time resolved detection, interferometric spectroscopy, optical coherence tomography, most optical pump/probe experiments, and other applications. Optical delay lines generally employ beam splitting optics to duplicate a pulse of light whereby one copy of the pulse is sent via a first optical path through one part of a system and the second copy is sent via a second optical path through a second part of the system that incorporates an optical delay arrangement such that the length of the second optical path can be changed in a controlled manner. A common optical delay technique reflects pulses of light off a moving retro-reflector mirror that is mounted on a motorized translation stage, such as a linear screw type translation stage, or on voice coils. Another technique is to simply stretch the optical fiber through which the pulses of light travel.

U.S. Pat. No. 5,220,463 to Edelstein et al. describes an optical delay line with opposite-facing hollow front surface retroreflectors that are offset to each other. A standard mechanical translating device that is connected to one of the retroreflectors adjusts the distance between the retroreflectors along a line of movement that is parallel to the reflected light beam as it enters and exits the retroreflectors. In one variation, a movable retroreflector is mounted on a linear slide that is constrained for movement in a straight line on a stage. A motor driven drive wheel links an eccentric pivot on the drive wheel with a pivot on the movable retroreflector. As the wheel rotates, the retroreflector moves back and forth in a generally sinusoidal fashion with respect to the stage so that the rotational motion of the wheel is translated into a linear motion. This optical delay line arrangement, which requires a relatively massive mirror to constantly stop and accelerate, is not suitable for applications that require both high amplitude and frequency.

One such application involves online measurements using terahertz (T-ray or THz) radiation, which lies on the boundary of electronics (millimeter waves) and photonics (infrared). The terahertz spectrum encompasses the wavelengths approximately in the range of 3 mm to 15 µm. Terahertz radiation exhibits a large range of modifications on passage through varying materials or on reflection from materials. Such changes include attenuation or partial attenuation of different frequencies of the waveform and other alteration of the waveform depending upon the material through which the radiation or pulses pass. Terahertz radiation interacts strongly with polar molecules, a prime example being water. Water molecules absorb terahertz waves, on the one hand limiting penetration of the radiation in moist substances, and on the other hand making it readily detectable even in very low concentrations. It can be used for detecting low concentrations of polar gases. However, terahertz radiation will penetrate non-polar substances such as fats, cardboard, cloth and plastics with little attenuation. Materials including organic materials have varying transmission, reflection and absorption characteristics to terahertz radiation. Accordingly, use of terahertz radiation can indicate the presence of different materials.

Typically, a terahertz time-domain spectroscopy setup has three major categories of components: optics components include the laser and optical-delay line; terahertz components include the emitter and detector; and control components that are used to modulate terahertz generation, synchronize the delay line, and perform data acquisition. Both the optical-delay and the optical modulator impose limits on the overall speed of the system. In a delay line used in terahertz time domain spectroscopy, the magnitude of the path length change affects the frequency range over which a measurement can be obtained and the repetition rate generally governs the time it takes to scan a frequency window. Higher repetition rates lead to more measurements per time period.

Since most moving displacement designs (other than fiber stretching) as exemplified by U.S. Pat. No. 5,220,463 operate on the principle of linear displacement of a mirror, conventional optical delay arrangements do not generate both high repetition rates and large displacements due to the high acceleration required. The art is in need of an optical delay system that affords both large amplitude and high frequency. In particular, commercial online scanning measurement systems would benefit from an optical delay configuration which can provide large displacement with a repetition rate that is faster than that which is currently available.

SUMMARY OF THE INVENTION

The present invention is based in part on the recognition that optical delay lines exhibiting large amplitude (displacement) and high frequency (repetition rate) can be developed by designing the retroreflector to be displaced along a circular path, rather than along a linear one, while being held in angular alignment with launch and return sources of light such as optical fibers. In particular, the retroreflector is pivotally mounted on a rotating element such that the optical axis of the retroreflector's motion is mobile so that its angle or position changes relative to a fixed observer. There is no linear stopping and starting of the retroreflector and all acceleration of retroreflector is rotational acceleration within small angles so that the required forces needed to operate the optical delay line are greatly reduced.

In one aspect, the invention is directed to an optical delay line that includes:

an elongated member having a retroreflector that is slidably mounted thereon, wherein the elongated member has a linear slot that defines a path through which the retroreflector moves and wherein the elongated member has on its proximal end a fixed pivot axis;

a launch optical fiber having a first end for introducing a light beam toward the retroreflector;

a return optical fiber having a first end for receiving a light beam that is reflected from the retroreflector;

a rotatable disk having a central rotation axis that is parallel to the fixed pivot axis of the elongated member and having a second pivot axis, that is parallel to the fixed pivot axis of the elongated member, wherein the retroreflector is attached to the rotatable disk such that rotation of the rotatable disk translates the retroreflector between a first end and a second end of the linear slot and rotation of the disk defines a circular path through which the second pivot axis travels; and means for rotating the rotatable disk.

In another aspect, the invention is directed to a dual rotating element optical delay line that includes:

an elongated member having a retroreflector that is slidably mounted thereon, wherein the elongated member has a linear slot that defines a path through which the retroreflector moves;

a launch optical fiber having a first end, for introducing a light beam toward the retroreflector, that is positioned at an proximal end of the elongated member;

a return optical fiber having a first end, for receiving a light beam that is reflected from the retroreflector, that is positioned at the proximal end of the elongated member;

a first rotatable disk having a first central rotation axis and a first pivot axis onto which the retroreflector is attached so that rotation of the first rotatable disk translates the retroreflector between a first end and a second end of the linear slot and rotation of the first disk defines a first circular path through which the first pivot axis travels;

a second rotatable disk having a second central rotation axis that is parallel to the first central rotation axis and a second pivot axis that is parallel to the second central rotation axis, wherein the second rotatable disk has the same diameter as that of the first rotatable disk and is offset by one disk diameter, wherein the first end of the launch optical fiber and the first end of the return optical fiber are positioned at the second pivot axis and wherein the first rotatable disk is coupled to the second rotatable disk for synchronized movement of the first and second rotatable disks and the retroreflector is oriented such that the reflected light beam is directed back along a direction, that is parallel to the longitudinal axis of the linear slot, toward the fixed pivot axis; and means for rotating the two rotatable disks such that the first rotatable disk rotates in a rotational direction that is opposite to that of the second rotatable disk.

In a further aspect, the invention is directed to an optical delay line, which employs free beam paths between the launch and return optics and the retroreflector, that includes:

an elongated member having a retroreflector that is slidably mounted thereon, wherein the elongated member has a linear slot that defines a path through which the retroreflector moves;

a pivotally mounted mirror that is positioned to reflect an input light beam towards the retroreflector and to reflect a return light beam from the retroreflector;

means for transmitting an input light beam towards the mirror along a first optical path;

means for receiving the return light beam that is reflected from the mirror along a second optical path;

a rotatable disk having a central rotation axis and a pivot axis wherein the retroreflector is attached to the rotatable disk such that rotation of the rotatable disk translates the retroreflector between a first end and a second end of the linear slot and rotation of the disk defines a circular path through which the pivot axis travels;

means for rotating the rotatable disk; and means for rotating the pivotally mounted mirror such that input light is reflected from a first area on the mirror and towards the retroreflector and the return light is reflected from a second area on the mirror and towards the means for receiving the return light.

DESCRIPTION OF PREFERRED EMBODIMENTS

Figure 1A:
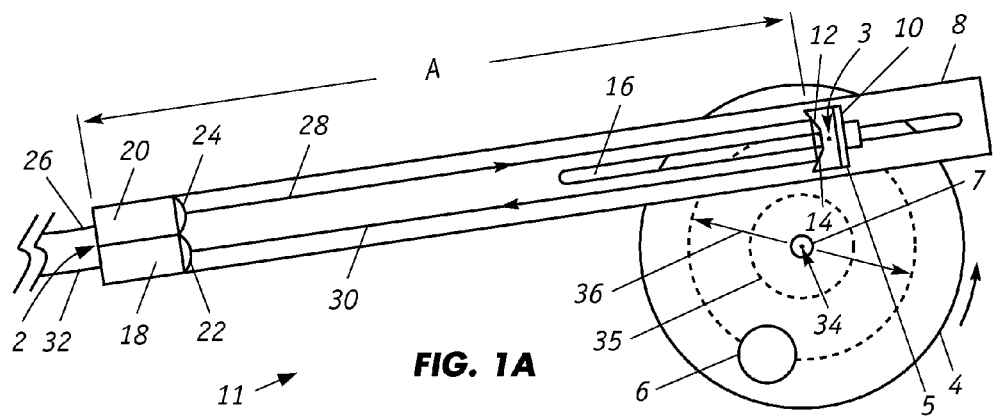
FIGS. 1A and 1B illustrate an optical delay line for fiber optic systems with a single rotating element.
Figure 1B:
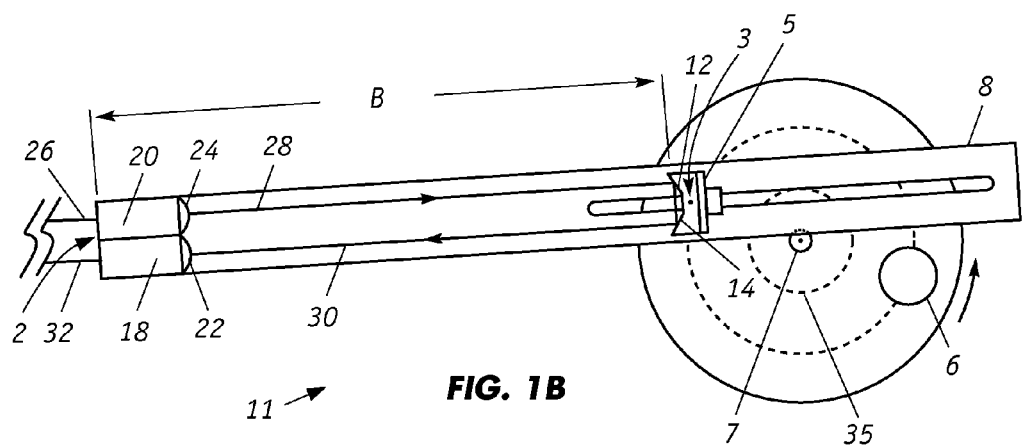

FIGS. 1A and 1B illustrate a rapid, cyclically variable, long delay length optical delay line apparatus 11 with reduced driving torque requirements. The apparatus employs optical fibers for source and return light paths to allow a retroreflection mirror on the apparatus to be displaced along a circular path, rather than on a linear one, while the mirror is held in angular alignment with the source and return optical fibers. Apparatus 11 includes an elongated alignment member (or alignment linkage) 8 with a linear guide slot 16 formed at the distal end. A stage 5, onto which retroreflector 10 is mounted, is constrained to only freely translate along the longitudinal axis (path) of linear guide slot 16. Retroreflector 10 has reflective surfaces 12 and 14. The opening of the linear guide slot 16 is preferably located in the plane that is defined by the two longest dimensions of elongated alignment member 8.

Secured at the proximal end of alignment member 8 are collimation lens assemblies 18 and 20, which include collimating lens 22 and 24, respectively. Launch or light source optical fiber 26 is coupled to collimation lens assembly 20 and light return optical fiber 32 is coupled to collimation lens assembly 18. The collimation lens assemblies 18, 20 are configured to rotate about fixed lens pivot axis 2 which has an axis that is perpendicular to the plane that is defined by the two longest dimensions of elongated alignment member 8. Collimating lenses 22 and 24 are aligned so that light 28 from light source optical fiber 26 impinges upon a selected spot on reflective surface 12 of retroreflector 10 and return light 30 that is reflected from reflective surface 14 impinges on lens 22. Retroreflector 10 is oriented such that reflected light is generally directed back along the direction of the longitudinal axis of the guide slot 16 towards lens pivot axis 2. As is apparent, alignment linkage 8 may be replaced by electromotive devices and controls to maintain angular alignment without physical linkage of the collimation lens assemblies to the retroreflector.

Optical delay line apparatus 11 further includes a rotatable disk 4 that has (i) a fixed central rotational axis 34 that is parallel to fixed lens pivot axis 2 and (ii) an eccentric mirror pivot axis 3, located near the edge of rotatable disk 4, which is also parallel to fixed rotational axis 34. A counter weight 6 is secured to the front surface of rotating disk 4 at a diametrically opposite point from mirror pivot axis 3 that is separated by inner diameter 36. A rotary encoder 7 can be incorporated with rotating disk 6 for motion feedback; alternatively, a linear encoder scale can be installed on alignment member 8. With the configuration of optical delay apparatus 11, the length of inner diameter 36 typically ranges from 0.5 to 10 cm and preferably from 1 to 5 cm and rotatable disk 4 rotates at from 0 to 10,000 rpm and preferably from 600 to 6,000 rpm.

In operation as shown in FIG. 1A, as motor 35 drives rotatable disk 4, retroreflector 10, which is mounted on a stage 5, is constrained to only freely translate along the longitudinal axis of linear guide slot 16 thereby maintaining substantial angular alignment with the longitudinal axis. Simultaneously, retroreflector 10 is only free to rotate about mirror pivot axis 3 of rotating disk 4, thereby retroreflector 10 moves in a constrained circular path, with its velocity and acceleration defined by the relative motions of linear guide slot 16 and mirror pivot axis 3. When rotatable disk 4 rotates at a constant speed, the retroreflector 10 exhibits a symmetrical sinusoidal displacement profile. The distance from the collimation lens assembly 20 to reflective surface 12 of retroreflector 10 is approximately equal to one-half the optical delay length. In the position of the optical delay line shown in FIG. 1A, this distance is designated "A".

As rotatable disk 4 continues along a circular path to the position shown in FIG. 1B, retroreflector 10 moves closer to collimation lens assemblies 18, 20 and the distance designated "B" is equal to about one-half that of the optical delay length. In one complete cycle or revolution of rotatable disk 4, the change in delay distance is equal to the optical delay length. During the continuous circular displacement of rotatable disk 4, the proximal end of elongated alignment member 8 rotates about fixed lens pivot axis 2 such that retroreflector 10 is held in angular alignment with light source optical fiber 26 and light return optical fiber 32. This is possible in part because of the flexible nature of the optical fibers.

Since retroreflector 10 has two reflective surfaces 12, 14, for this optical delay apparatus, the average optical delay length can be defined as the average between the maximum and minimum distances from the collimation lens assembly 20 and reflective surface 12, multiplied by two. As is apparent, more mirrors can be employed to increase this multiplier to 4 times or more. For instance, two retroreflectors that are positioned so that a light beam is reflected between them a plurality of times parallel to the optical axis can be employed. This arrangement is described in U.S. Pat. No. 5,220,463 to Edelstein et al., which is incorporated herein by reference. Multipass optical retroreflectors with multiple reflecting surfaces are described in U.S. Pat. No. 6,979,088 to Currie, which is incorporated herein by reference.

Figure 2A:
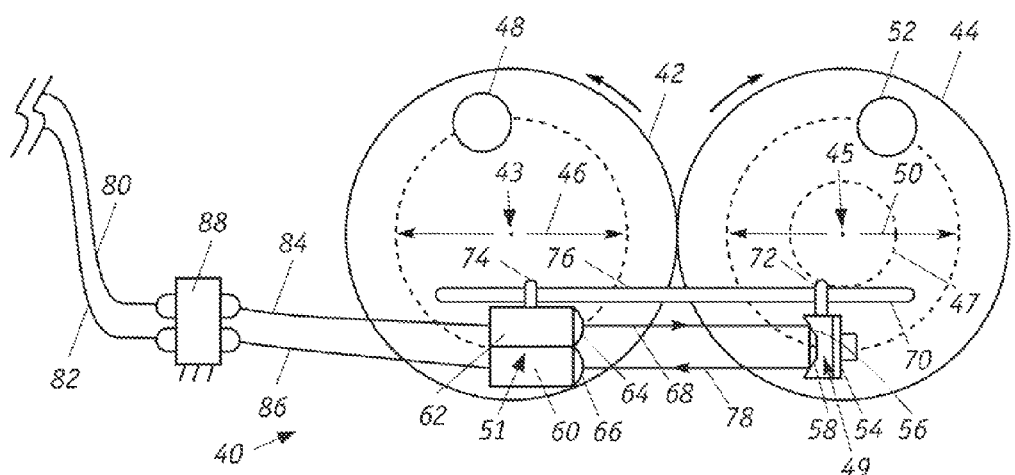
FIGS. 2A and 2B illustrate an optical delay line for fiber optic systems with dual rotating elements.
Figure 2B:
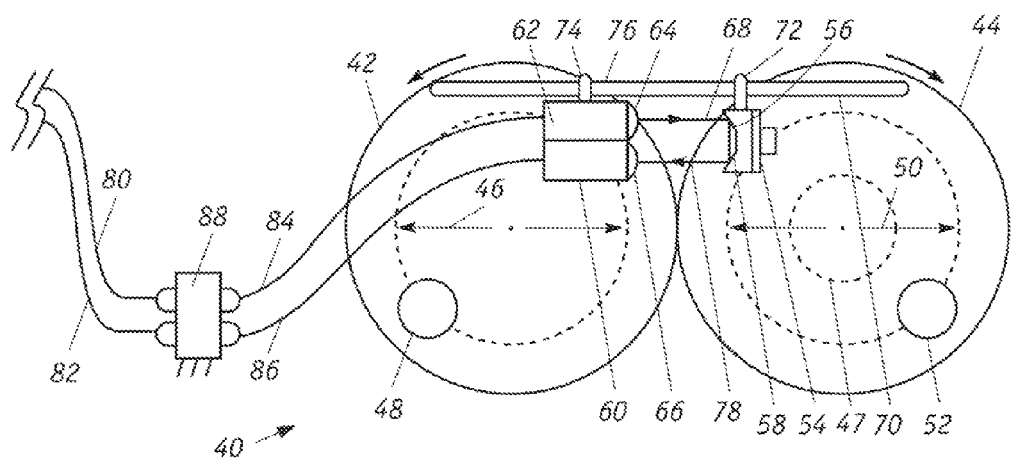

FIGS. 2A and 2B depict an optical delay line apparatus 40, that is also particularly suited for fiber optic systems, and which employs dual rotating elements. Apparatus 40 includes rotatable disks 42 and 44 that have the same outer diameter and rotate at the same speed but in opposite directions. Each of Rotatable disks 42, 44 can be driven by separate motors for synchronized rotation. Preferably, each rotatable disk has linkages that mesh so that rotating one disk by one motor 47 effectively rotates the other at the same speed as well. Each rotatable disk, for example, can comprise a tooth wheel.

Rotatable disk 42 has a fixed central rotational axis 43 and an eccentric lens pivot axis 51, located near the edge of rotatable disk 42, where collimation lens assemblies 60 and 62 are pivotally mounted. A counter weight 48 is secured to the front surface of rotating disk 42 at a diametrically opposite point from lens pivot axis 47 that is separated by inner diameter 46. Similarly, rotatable disk 44 has a fixed central rotational axis 45 and an eccentric mirror pivot axis 49, located near the edge of rotatable disk 44, where retroreflector 54 is pivotally mounted. A counter weight 52 is secured to the front surface of rotating disk 44 at a diametrically opposite point from mirror pivot axis 49 that is separated by inner diameter 50, which preferably has the same as length as inner diameter 46.

Optical delay apparatus 40 further includes an elongated alignment member 70 with a linear guide slot 76 onto which retroreflector 54 is slidably mounted via moveable hanger device 72 so as to be constrained to only freely translate along the longitudinal axis (path) of linear guide slot 76. Retroreflector 54 has reflective surfaces 56 and 58. Collimation lens assemblies 60 and 62, which include collimating lens 66 and 64, respectively are slidably mounted via moveable hanger device 74 at the proximal end of alignment member 70.

Launch or light source optical fiber 84 is coupled to collimation lens assembly 62 and light return optical fiber 86 is coupled to collimation lens assembly 60. In use, the source of light pulses may be quite some distance from the optical delay apparatus so a stationary fiber optic coupling device 88 can be employed to connect source fiber optic cable 80 and return fiber optic cable 82 to light source optical fiber 84 and light return source optical fiber 84, respectively.

Collimating lenses 64 and 66 are aligned so that light 68 from light source optical fiber 84 impinges upon a selected spot on reflective surface 56 of retroreflector 54 and return light 78 that is reflected from reflective surface 58 impinges on lens 66. Retroreflector 54 is oriented such that reflected light is generally directed back along the direction of the longitudinal axis of the guide slot 76 towards lens pivot axis 47. As is apparent, a retroreflector with more than 2 mirrors, or multiple retroreflectors, can be employed.

As rotatable disks 42 and 44 rotate, the optical distance between collimating lenses 64, 66 to reflective surfaces 58 and 58, respectively, changes. The optical distance for the apparatus as shown in FIG. 2B is closer than that shown in FIG. 2A. As a result of this synchronized movement, retroreflector 54 exhibits a symmetrical sinusoidal displacement profile. One feature of dual element optical delay apparatus 40, in which collimation lens assemblies 60, 62 rotate counter-clockwise with rotatable disk 42 while retroreflector 56 simultaneously rotates clockwise with rotatable disk 44, is that the diameters of the rotatable disks used can be smaller than the single rotatable element used in apparatus 11 (FIG. 1A). In other words, in order to achieve the same optical delay length, the size of each of the rotatable disks in the dual rotating element apparatus can be significantly smaller than that of the rotatable disk single the rotatable element apparatus. Each of inner diameter 46 in rotatable disk 42 and inner diameter 50 typically has a length that ranges from 0.2 to 5 cm and preferably from 0.5 to 2.5 cm and each of rotatable disks 42 and 44 rotates at from 0 to 10,000 rpm and preferably from 600 to 6,000 rpm.

Figure 3A:
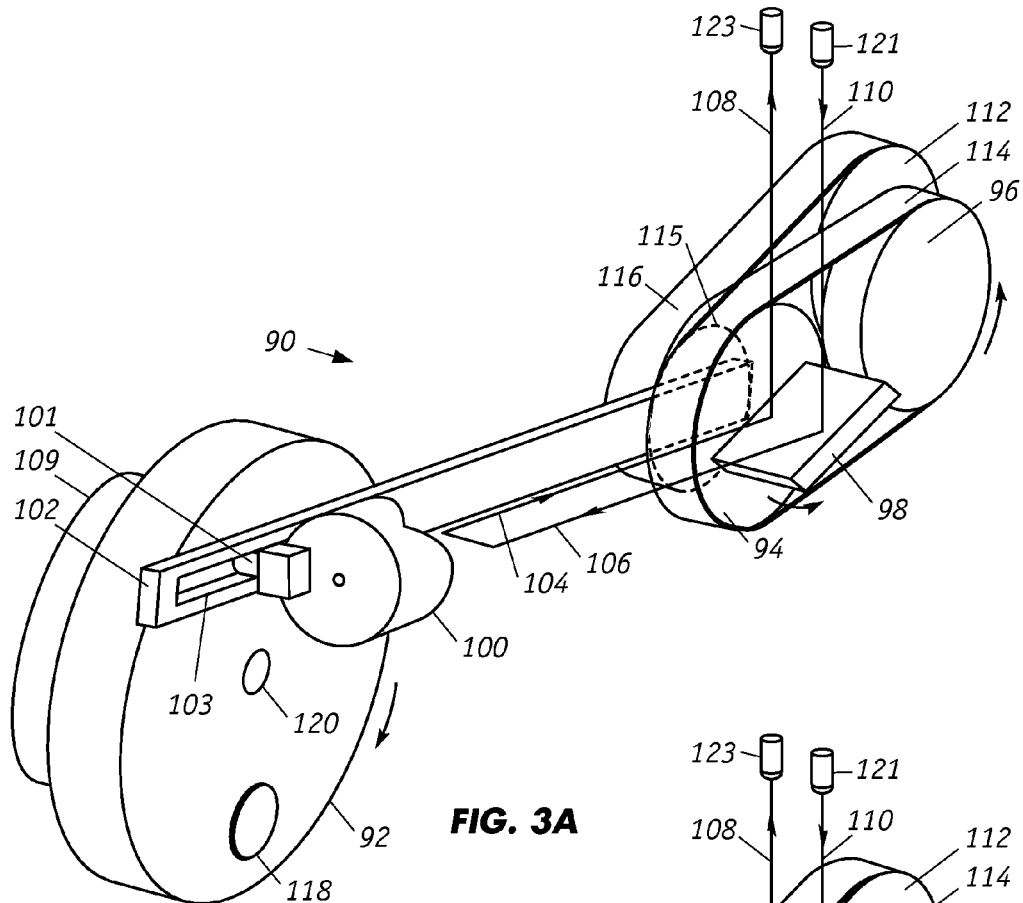
FIGS. 3A, 3B, and 3C illustrate an optical delay line that is characterized by free space light beams.

FIG. 3A illustrates an optical delay line apparatus 90 which is suitable for free space light beams, that is, where the source and return light paths are not confined within optical fibers. Apparatus 90 includes motor 109, a motor driven rotatable disk 92 having a fixed central rotational axis 120, and an elongated alignment member 102 with a linear guide slot 103 formed at the distal end. Stage 101 is attached to the surface of rotatable disk 92 at an eccentric mirror pivot axis located near the edge of rotatable disk 92. Stage 101 is positioned within linear guide slot 103 so as to be constrained to only freely translate along its longitudinal axis. A retroreflector mirror 100 is mounted to stage 101. A counter weight 118 is attached at a diametrically opposite point from stage 101; the distance in between is referred to as the inner diameter of rotatable disk 92. The length of linear guide slot 103 is at least equal to that of the inner diameter so that stage 101 so that stage 101 aligned with member 102 throughout the rotation of disk 92. The inner diameter in rotatable disk 92 typically has a length that ranges from 0.5 to 10 cm and preferably from 1 to 5 cm and rotatable disk 92 at from 0 to 10,000 rpm and preferably from 600 to 6,000 rpm.

Apparatus 90 further includes a plane mirror 98 that is positioned adjacent the proximal end of elongated alignment member 102 so that the reflective surface of retroreflector 100 faces plane mirror 98. Retroreflector 100 can comprise more than two mirrors to increase the optical delay length or multiple retroreflectors can be employed. Light source beam 110 is directed towards mirror 98 such that reflected light beam 106 is redirected towards retroreflector 100. Similarly, reflected return light beam 104 from retroreflector is redirected by mirror 98 as output beam 108. Light source beam 110 can be irradiated towards mirror 98 through a stationary collimation lens 121 so that the path of light source beam 110 remains constant. In this arrangement, output beam 108 is directed back from mirror 98 in the same direction as the axis of light source beam 110 and is captured by collection lens 123.

Plane mirror 98 is designed for coordinated movement with retroreflector 100 so the optical paths of light source beam 110 and output beam 108 remain constant during operation of optical delay apparatus 90. In particular, the distal end of elongated alignment member 102 is operatively coupled to a 2:1 timing belt driven gear reduction apparatus so that mirror 98 pivots about the axis at one-half the angle at which retroreflector rotates. Timing belt 116 is looped around gear 112 and gear (pinion) 115, which have a gear ratio of 2:1. Elongated alignment member 102 is affixed to and drives gear 115. Gears 94 and 96 are the same size and have timing belt 114 being looped around them. Gear 96 is coupled to gear 112 and plane mirror 98 is pivotally mounted on gear 94 about an axis that is collinear to gear 115. The motion of elongated alignment member 102 drives timing belt 116 in the appropriate direction in coordination with rotatable disk 92 so that the optical paths of free space light source beam 110 and free space output beam 108 remain constant.

In operation, as motor 109 drives rotatable disk 92 to rotate clockwise, retroreflector 100 which is mounted on stage 101 is constrained to only freely translate along the longitudinal axis (path) of linear guide slot 102 thereby maintaining substantial angular alignment with the longitudinal axis. Simultaneously, retroreflector 100 is only free to rotate about mirror pivot axis 120 of rotating disk 92, thereby retroreflector 100 moves in a constrained circular path, with its velocity and acceleration defined by the relative motions of linear guide slot 103 and mirror pivot axis 120. When rotatable disk 92 rotates at a constant speed, the retroreflector 110 exhibits a symmetrical sinusoidal displacement profile. The distance from the collimation lens 121 to a reflective surface of retroreflector 110 is approximately equal to one-half the optical delay length. The change in delay length is then equal to twice the change in distance from retroreflector 100 to mirror 98 as disk 92 rotates through a complete revolution, which is equivalent to the diameter at which retroreflector 100 is mounted to disk 92.

Figure 3B:
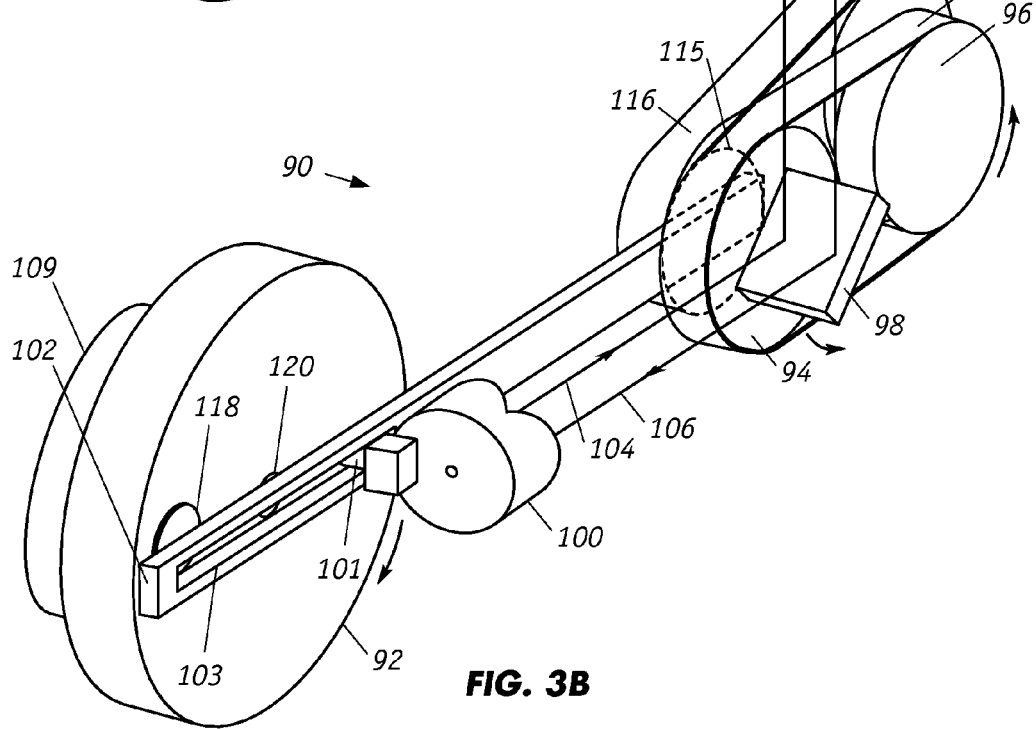
Figure 3C:
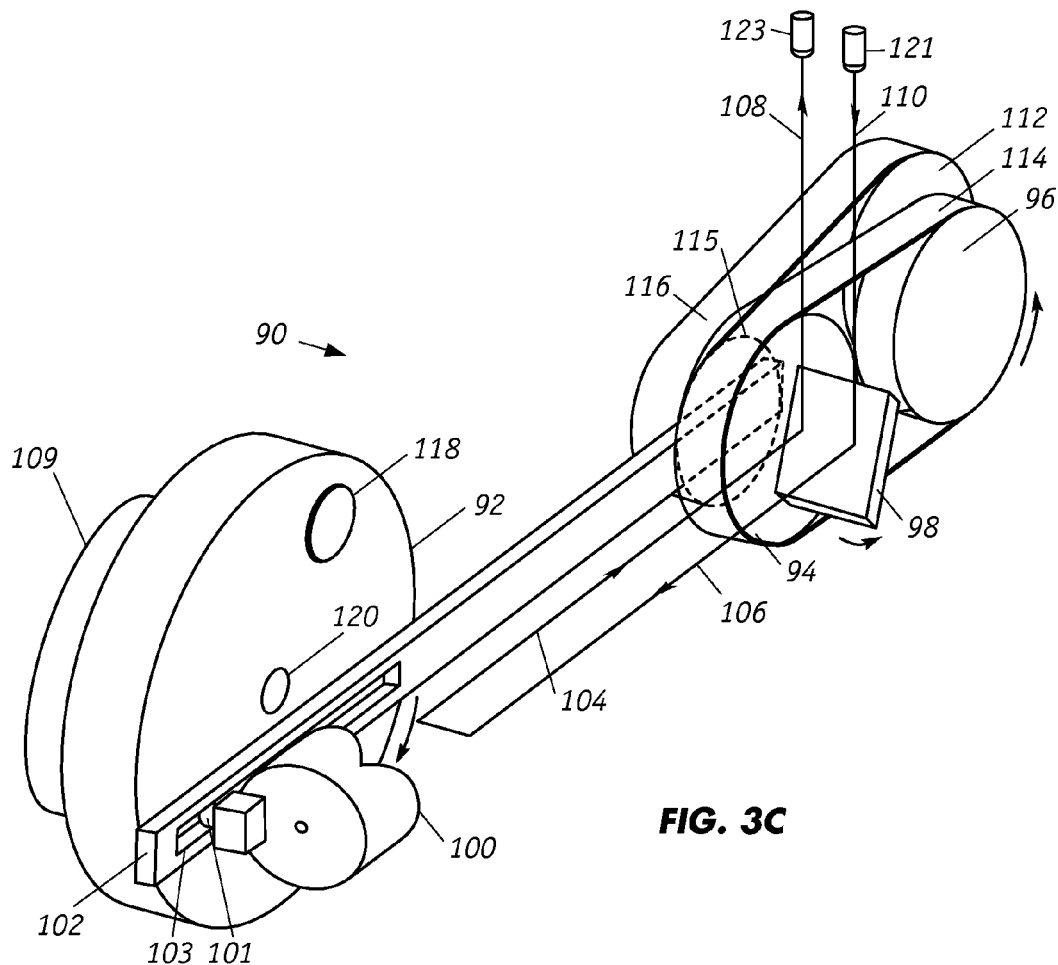

As rotatable disk 92 continues along its circular path, plane mirror 98 moves in synchronized fashion so that the path of light source beam 110 remains optically aligned with mirror 98 and the paths of input beam 110 and output beam 108 do not change. In particular, as retroreflector 100 moves from its position initial position depicted in FIG. 3A to those shown in FIGS. 3B and 3C, the angle of incidence light source beam 110 on plane mirror 98 increases in order to maintain the optical alignment. Once retroreflector 100 reaches the lowest point along its circular path, FIG. 3C, and begins to rise, belt 114 reverses direction to cause mirror 98 to move in the opposite direction, decreasing angle of incident keeping optical alignment of paths 110 and 108 with retroreflector 100.

Figure 4:
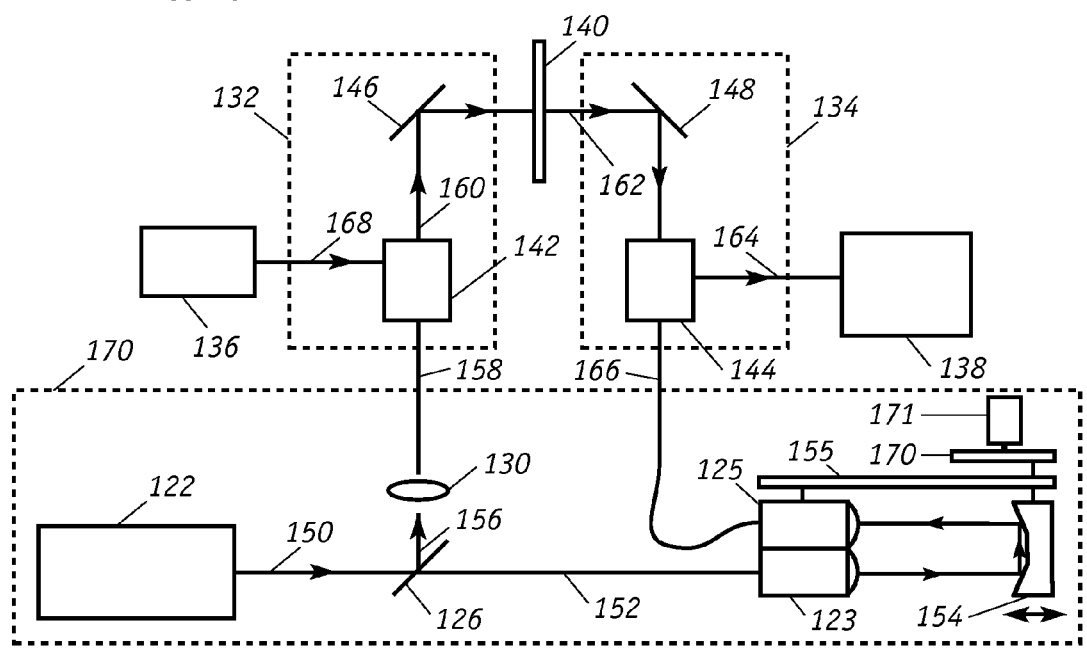
FIG. 4 illustrates a scanning terahertz sensor system employing an optical delay line.

FIG. 4 shows the structure of a terahertz time-domain spectrometer for monitoring at least one property of the moving sheet or web of material 140. The basic components of the spectrometer include: pulsed laser source 122, beam splitter 126, terahertz transmitter 142, modulated power source 136, terahertz receiver or detector 144, spectroscopic analyzer 138 and an optical delay device that includes retroreflector 154. Pulsed laser source 122, such as a femto-second pulse laser, generates pump signals 150 that are directed toward beam splitter 126 that splits the light pulses of pump signal 150 to yield excitation light 156 and detector gating light 152.

Excitation light 156 is focused by objective lens 130 and launched into and transmitted through delivery optical fiber 158. Excitation light 156 illuminates transmitter 142 to generate terahertz radiation or T-rays 160 which are directed by mirror 146 into moving sheet 140. Modulated power source 136 supplies an electrical input 168 into terahertz transmitter 142. T-rays 162 which emerge from moving sheet 140 are reflected from mirror 148 and captured by detector 144. Mirrors 146 and 148 when employed are typically off-axes parabolic mirrors.

Detector gating light 152 is directed to optical delay device which serves to set or modify the difference between the timing of the detector gate light 152 and the timing of the excitation light 156. The optical delay device can comprise any of the inventive optical delay devices such as apparatus 11 depicted in FIGS. 1A and 1B. As shown in FIG. 4, the device includes an elongated alignment member 155 that has a linear guide slot formed at the distal end. Collimation lens assemblies 125, 123 are secured at the proximal end of alignment member 155 while a retroreflector 154 is secured to a rotatable disk 170 through the linear guide slot in alignment member 155. Collimation lens assemblies 125 and 123 are in optical alignment with retroreflector 154 so that as motor 171 drives rotatable disk 170, changes the length of the optical path of detector gating light 152, thereby changing and setting the difference between excitation light irradiation timing (T-ray generating timing) and the detector gating light irradiation timing (T-ray detecting timing). The optical delay device launches light into delivery optical fiber 166 and into receiver or detector 144. The laser pulses that exit from the end of optical fiber 166 are used to effectively switch on the terahertz receiver in a synchronous detection scheme. When the arrival time of these synchronizing pulses to the terahertz receiver are varied, the terahertz pulses can be traced out. The output 164 from receiver 144 is an electrical signal that is typically amplified and digitized and then read into a computer for analysis or alternatively the electrical signal can be analyzed in a digital signal processor. The electrical signal can be amplified with a transimpedance amplifier and then fed into a lockin amplifier. If lockin detection is employed, a modulated bias voltage is typically applied to power source 136. The lockin detector is then synchronized with this bias modulation.

Detector 144 generates detection signals 164 which are transmitted to spectroscopic analyzer 138. The electrical signals generated by the detector that can be analyzed in the computer in the temporal or frequency domain. For instance, this analysis can also be done in a Field-Programmable Gate Array (FPGA) or a Digital Signal Processor (DSP).

While the optical delay device is positioned in optical path of detector light 152, an optical delay device could be positioned in the optical path of excitation light 156 instead. Preferably, laser source 122, beam splitter 126, the optical delay device are housed in compartment 170. In a transmission mode embodiment, terahertz transmitter 142 and mirror 144 are located in sensor head 132 whereas detector 144 and mirror 148 are located in sensor head 134. The sensor head can be any suitable light weight structure housing the associated components.

If optical rectification is used to generate or detect the THz radiation, then optical fibers are preferably selected from those which can maintain the linear polarization state of the light which is injected into them since the THz transmitter and receiver are dependent upon the polarization state of the pump light. Preferred optical fibers are highly birefringent or single polarization photonic bandgap fiber which will maintain the polarization of the femto-second pulse laser generated pulses of light. It is often preferable to use a THz antenna to both generate and receive the THz radiation, in which case, using non-polarization maintaining optical fibers are preferred since the generation and detection of the THz radiation is not polarization sensitive.

In order to function as a scanning terahertz sensor, sensor heads 134 and 132 must be mobile which means that movement of optical fibers 158 and 166, which are in optical communication with sensor heads 132 and 134, respectively, must also be accommodated. Optical fibers 158 and 166 can be routed through take-up mechanisms to control the bending of the optical fibers, as further described in US Patent Application No. 20060109519 to Beselt et al., which is incorporated herein by reference.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

The invention claimed is:

1. An optical delay line that comprises:
an elongated member having a retroreflector that is slidably mounted thereon, wherein the elongated member defines a linear path through which the retroreflector moves and wherein the elongated member has on its proximal end a fixed pivot axis;
a launch optical fiber having a first end for introducing a light beam toward the retroreflector;
a return optical fiber having a first end for receiving a light beam that is reflected from the retroreflector;
a rotatable disk having a central rotation axis that is parallel to the fixed pivot axis of the elongated member and having a second pivot axis, that is parallel to the fixed pivot axis of the elongated member, wherein the retroreflector is attached to the rotatable disk such that rotation of the rotatable disk translates the retroreflector between a first end and a second end of the linear slot and rotation of the disk defines a circular path through which the second pivot axis travels; and
means for rotating the rotatable disk.

2. The optical delay line of claim 1 wherein the elongated member has a plane that is defined by the two longest dimensions of the elongated member and the linear path is parallel to the longitudinal axis of the elongated member.

3. The optical delay line of claim 2 wherein the retroreflector is simultaneously constrained to (i) translate along the linear path thereby maintaining substantial angular alignment with the longitudinal axis of the linear slot and constrained to (ii) rotate along the circular path that is defined by the second pivot axis such that the retroreflector's velocity and acceleration are defined by the relative motion of the elongated member and the second pivot axis.

4. The optical delay line of claim 3 wherein the first end of the launch optical fiber and the first end of the return optical fiber are positioned at the proximal end of the elongated member and the retroreflector is oriented such that the reflected light beam is generally directed back along a direction, that is parallel to the longitudinal axis of the linear slot, toward the fixed pivot axis.

5. The optical delay line of claim 4 wherein the first end of the launch optical fiber terminates at a first collimator and the first end of the return optical fiber terminates at a second collimator and wherein the first and second collimators are secured substantially at the fixed pivot axis and are aligned so that light from the launch optical fiber impinges a selected spot on the retroreflector and return light reflected therefrom impinges upon the second collimator.

6. The optical delay line of claim 1 comprising a counterweight that is attached on the same face of the rotating disk on which the retroreflector is attached and at a diametrically opposite point from the second pivot axis of the rotating disk.

7. The optical delay line of claim 1 wherein a change in delay distance which is measured from the first end of the launch source optical fiber to the retroreflector ranges from 0.5 to 10 cm.

8. The optical delay line of claim 1 wherein the means for rotating the rotatable disk moves the rotatable disk at about 0 to 6,000 rpm.

9. An optical delay line that comprises:
an elongated member having a retroreflector that is slidably mounted thereon, wherein the elongated member defines a linear path through which the retroreflector moves;
a launch optical fiber having a first end, for introducing a light beam toward the retroreflector that is positioned at a proximal end of the elongated member;
a return optical fiber having a first end, for receiving a light beam that is reflected from the retroreflector, that is positioned at the proximal end of the elongated member;
a first rotatable disk having a first central rotation axis and a first pivot axis onto which the retroreflector is attached so that rotation of the first rotatable disk translates the retroreflector between a first end and a second end of the linear slot and rotation of the first disk defines a first circular path through which the first pivot axis travels;
a second rotatable disk having a second central rotation axis that is parallel to the first central rotation axis and a second pivot axis that is parallel to the second central rotation axis, wherein the second rotatable disk has the same diameter as that of the first rotatable disk and is offset by one disk diameter, wherein the first end of the launch optical fiber and the first end of the return optical fiber are positioned at the second pivot axis and wherein the first rotatable disk is coupled to the second rotatable disk for synchronized movement of the first and second rotatable disks and the retroreflector is oriented such that the reflected light beam is directed back along a direction, that is parallel to the longitudinal axis of the linear slot, toward the fixed pivot axis; and
means for rotating the two rotatable disks such that the first rotatble disk rotates in a rotational direction that is opposite to that of the second rotatable disk.

10. The optical delay line of claim 9 wherein the first rotatable disk defines a first plane and the second rotatable disk defines a second plane that is coplanar with the first plane.

11. The optical delay line of claim 9 wherein the first and second rotatable disks are coupled by gears and the means for rotating the two rotatable disks comprises a motor that is coupled to the first rotatable disk or the second rotatable disk.

12. The optical delay line of claim 9 wherein the retroreflector is simultaneously constrained to (i) translate along the linear path thereby maintaining substantial angular alignment with the longitudinal axis of the linear path and free to (ii) rotate about the second pivot axis thereby moving in a constrained path such that the retroreflector's velocity and acceleration are defined by the relative motion of the elongated member and the second pivot axis.

13. The optical delay line of claim 9 wherein the first end of the launch optical fiber terminates at a first collimator and the first end of the return optical fiber terminates at a second collimator and wherein the first and second collimators are secured substantially at the second pivot axis and are aligned so that light from the launch optical fiber impinges a selected spot on the retroreflector and return light reflected therefrom impinges upon the second colliminator.

14. The optical delay line of claim 9 comprising a first counterweight that is attached on the same face of the first rotating disk on which the retroreflector is attached and at a diametrically opposite point from the first pivot axis of the first rotating disk and a second counterweight that is attached on the same face of the second rotating disk on which the first and second collimators are attached and at a diametrically opposite point from the second pivot axis of the second rotating disk.

15. The optical delay line of claim 9 wherein a change in delay distance which is measured from the first end of the light source optical fiber to the retroreflector ranges from 0.2 to 5 cm.

16. The optical delay line of claim 9 wherein the means for rotating the rotatable disk moves the first and second rotatable disks at about 0 to 6,000 rpm.

17. An optical delay line that comprises:
an elongated member having a retroreflector that is slidably mounted thereon, wherein the elongated member defines a path through which the retroreflector moves;
a pivotally mounted mirror that is positioned to reflect an input light beam towards the retroreflector and to reflect a return light beam from the retroreflector; means for transmitting an input light beam towards the mirror along a first optical path;
means for receiving the return light beam that is reflected from the mirror along a second optical path;
a rotatable disk having a central rotation axis and a pivot axis wherein the retroreflector is attached to the rotatable disk such that rotation of the rotatable disk translates the retroreflector between a first end and a second end of the linear path and rotation of the disk defines a circular path through which the pivot axis travels;
means for rotating the rotatable disk; and
means for rotating the pivotally mounted mirror such that input light is reflected from a first area on the mirror and towards the retroreflector and the return light is reflected from a second area on the mirror and towards the means for receiving the return light.

18. The optical delay line of claim 17 wherein the retroreflector is simultaneously constrained to (i) translate along the linear path thereby maintaining substantial angular alignment with the longitudinal axis of the linear path and free to (ii) rotate about the pivot axis thereby moving in a constrained path such that the retroreflector's velocity and acceleration are defined by the relative motion of the elongated member and the pivot axis.

19. The optical delay line of claim 17 comprising a counterweight that is attached on the same face of the rotating disk on which the retroreflector is attached and at a diametrically opposite point from the pivot axis of the rotating disk.

20. The optical delay line of claim 17 wherein the pivotally mounted mirror is mounted about an axis that is substantially parallel to that of the central rotation axis of the rotatable disk.

* * * * *